(12) United States Patent
Brauss

(10) Patent No.: US 6,721,393 B1
(45) Date of Patent: Apr. 13, 2004

(54) X-RAY DIFFRACTION APPARATUS AND METHOD

(75) Inventor: Michael Brauss, Amherstburg (CA)

(73) Assignee: Proto Manufacturing Ltd., Oldcastle (CA)

(*) Notice: Subject to any disclaimer, the term of this patent is extended or adjusted under 35 U.S.C. 154(b) by 0 days.

(21) Appl. No.: 09/539,346

(22) Filed: Mar. 31, 2000

Related U.S. Application Data

(60) Provisional application No. 60/127,219, filed on Mar. 31, 1999.

(51) Int. Cl.[7] .............................. G01N 23/20; H05G 1/02
(52) U.S. Cl. .............................. 378/71; 378/72; 378/76; 378/79; 378/196; 378/197
(58) Field of Search .............................. 378/44, 45, 50, 378/59, 60, 64, 71, 72, 76, 79, 81, 196, 197, 70, 75, 195, 198

(56) References Cited

U.S. PATENT DOCUMENTS

| | | | | |
|---|---|---|---|---|
| 3,445,655 A | * | 5/1969 | Curry .......................... | 378/171 |
| 3,868,506 A | * | 2/1975 | Orgiso .......................... | 378/72 |
| 4,095,103 A | | 6/1978 | Cohen et al. ................ | 378/197 |
| 4,283,629 A | * | 8/1981 | Habermehl et al. ............ | 378/4 |
| 4,686,631 A | * | 8/1987 | Ruud .......................... | 702/42 |
| 4,807,273 A | | 2/1989 | Haendle ...................... | 378/116 |
| 5,054,043 A | | 10/1991 | Lucas et al. ................... | 378/86 |
| 5,073,912 A | * | 12/1991 | Kobayashi et al. ........... | 378/34 |
| 5,125,016 A | * | 6/1992 | Korhonen et al. ............ | 378/72 |
| 5,148,458 A | * | 9/1992 | Ruud .......................... | 378/72 |
| 5,490,195 A | | 2/1996 | Berkley ....................... | 378/70 |
| 5,614,720 A | * | 3/1997 | Morgan et al. .......... | 250/360.1 |
| 5,625,664 A | | 4/1997 | Berkley ....................... | 378/72 |
| 5,636,259 A | * | 6/1997 | Khutoryansky et al. .... | 378/197 |
| 6,007,243 A | * | 12/1999 | Ergun et al. ................ | 378/197 |
| 6,609,826 B1 | * | 8/2003 | Fujii et al. ................... | 378/198 |
| 6,618,465 B2 | * | 9/2003 | Mohr et al. .................... | 378/58 |

* cited by examiner

*Primary Examiner*—David V. Bruce
*Assistant Examiner*—Allen C Ho
(74) *Attorney, Agent, or Firm*—Fitch, Even, Tabin & Flannery

(57) ABSTRACT

An x-ray diffraction apparatus and method are provided in which an x-ray or goniometer head can be adjusted in different directions to allow the head to direct x-rays at a part from various positions. In this manner, stress measurements can be taken from a wider region of the part without requiring that the part itself be moved or that an operator move the unit, which can be relatively heavy. Preferably, the apparatus is a portable unit including adjustment mounts to allow the x-ray head to be moved in the different directions so that it can be transported for use in the field at the site at which a part is located to allow for measurements to be taken from the part while it remains in service.

16 Claims, 13 Drawing Sheets

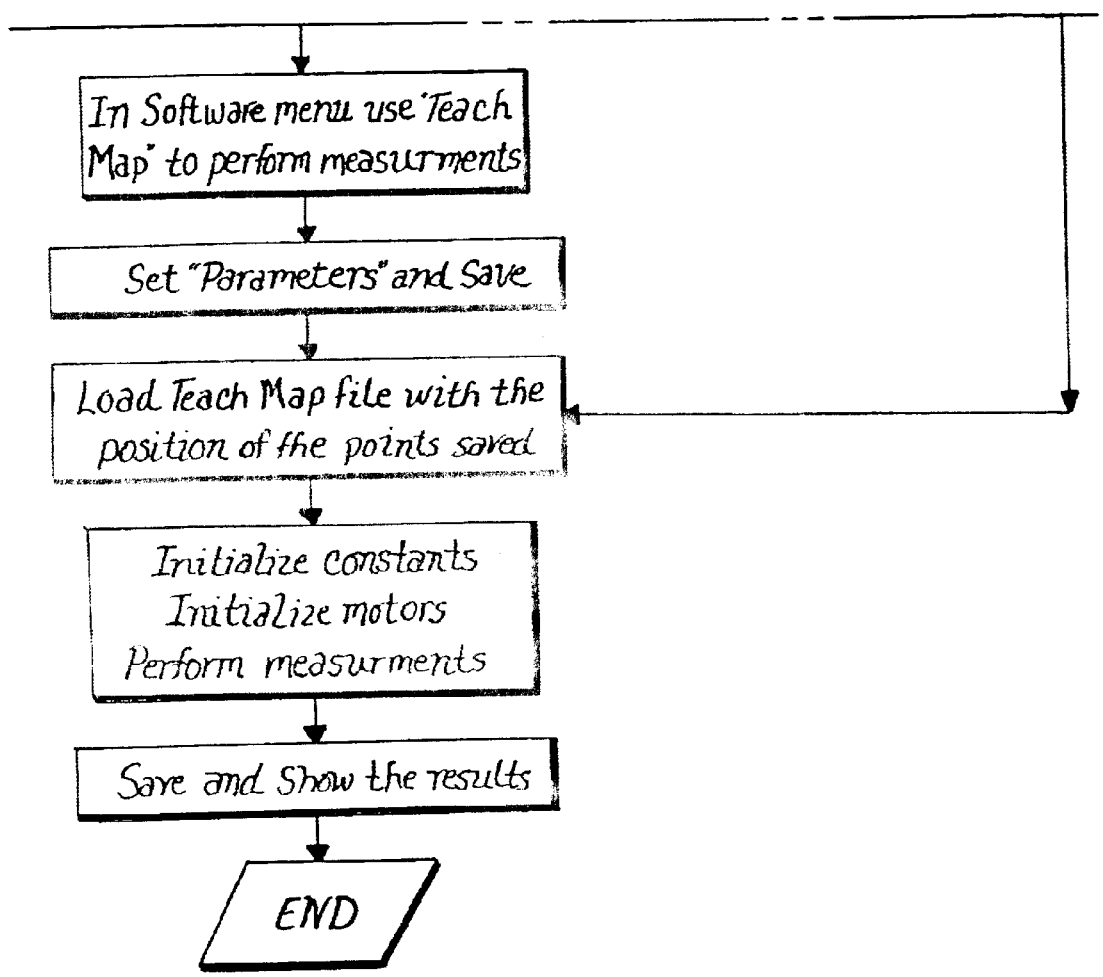

Fig. 13A Weld Fusion Zone

X-RAY DIFFRACTION APPARATUS AND METHOD

This application claims the benefit of Provisioned application Ser. No. 60/127,219, filed Mar. 31, 1999.

FIELD OF THE INVENTION

The invention relates to an apparatus and method for measuring strength related characteristics of a part using x-ray diffraction techniques and, more particularly, to an apparatus and method for measuring the strength related characteristics at a variety positions on the part.

BACKGROUND OF THE INVENTION

The use of x-ray diffraction techniques for measuring residual stresses in crystalline substances such as metal or ceramic materials is well-known. The general idea with the use of x-ray diffraction is to subject the material to the radiation of x-rays with the resulting sensed x-ray diffraction peak interpreted to arrive at a measurement of a strength related characteristic, i.e. stress, retained austenite, hardness of the part material, to show, for instance, the level of fatigue in the material. While using coupons or removing the part from service for measurement by x-ray diffraction laboratory equipment is done, neither is particularly satisfactory in that coupons require a portion of the part to be removed therefrom, and removing a part to be measured from service can create undue downtime along with the requisite labor for removal and replacement of the part back into service.

Accordingly, there is a need for portable x-ray diffraction equipment that can be used in the field at the site at which a part is located and without requiring the part to be removed from service. Portable x-ray diffraction equipment is known, however, some of these units suffer from great bulk making them less than ideal for use in field conditions. A further shortcoming with known x-ray diffraction equipment lies in the limitations in moving the goniometer head so that measurements can be taken across a sufficient number of positions on the part to obtain meaningful information therefrom, particularly where the part being tested has been used in the field where corrosion and other environmental use conditions can cause highly localized variations in the strength characteristic being determined. When the only measurements taken are those including such localized aberrations, the determination of what the remaining useful life of the part is before it needs to be retired to avoid fatigue failure thereof can be compromised.

In the laboratory setting this shortcoming requires periodic operator intervention to shift the part being measured so that the goniometer head is in position to direct x-rays at different positions thereon. As is apparent, such operator intervention is time consuming and labor intensive. In the field with current portable units, an operator generally has to physically shift the x-ray diffraction unit including the goniometer head along the part to the different positions at which measurements are desired. In either instance, there is significant operator intervention that is required which is undesirable. In addition, a portable x-ray diffraction unit is needed that can take measurements from complexly-shaped, parts and preferably without having to remove them from service while also providing an easy to interpret readout of the results of the measurements to show variations in the fatigue of the part in the region thereof that is measured.

In this regard, currently there is no means available to directly and quantitatively measure the total strain and hence be able to calculate the total stress non-destructively, the dead load strain and hence the dead load stress on the following: wire rope and/or single strand and/or multi-strand cables once they are installed on a structure or component. In addition there is no technique which can determine the strains on individual strands which may comprise a cable bundle or wire rope.

It would be desirable to be able to measure the total strain and hence determine the total stress on these types of load bearing members. Total strain is the residual strain plus the restraint strain plus the applied strain. Accordingly, the total strain relates to a material's remaining capacity to bear a load which is information that is particularly useful for load bearing structures for a number of safety and economic reasons.

Similarly, it would be desirable to be able to measure the dead load strain and hence dead load stress, which is the strain as a result of the weight and restraint stain of the structure or component without the strain due to the intended carrying load.

Another problem is that currently there is no means available to directly, accurately and non-destructively track the changes in wire rope and cable strain due to corrosion, creep, fatigue, overload etc.

A further problem is that currently there is no means available to directly and quantitatively and non-destructively measure the strain and hence be able to calculate the stress on the following: wire rope and or single strand and or multi-strand cables installed on an existing structure or component.

Despite the widespread use of cables, there are few tools available to inspect and characterize the stresses on cables. In fact, at this time there are two techniques currently in common use, a direct measurement by "jacking", literally by deflecting the cable with a calibrated jack and an indirect method using the "time to damping" of an induced vibration. Both of these approaches to stress measurement are at best an approximation of cable force due to underlying assumptions as discussed in F. A. Zahn and B. Bitterli's paper "Developments in Non-Destructive Stay Cable Inspection Methods" delivered at the IABSE Symposium in San Francisco in August, 1995 (see pp. 861–866). This is because the accuracy of the measurement is less than ideal, the total stress in the cable is ignored and the techniques cannot characterize individual strands which may comprise a cable bundle. Accordingly, there is a need for an apparatus and method that can address these shortcomings.

SUMMARY OF THE INVENTION

In accordance with the present invention, an x-ray diffraction apparatus and method are provided in which an x-ray or goniometer head can be adjusted in different directions to allow the head to direct x-rays at a part from various positions. In this manner, measurements can be taken from a wider region of the part without requiring that the part itself be moved or that an operator move the unit, which can be relatively heavy. In one aspect, the head can be rotated about its internal axis so that it can more readily direct x-rays along curved surfaces of parts while keeping a substantially constant distance therefrom. It is preferred that the apparatus be a portable unit including adjustment mounts to allow the x-ray head to be moved in the different directions so that it can be transported for use in the field at the site at which a part is located. In this instance, the unit allows for measurements to be taken from the part while it remains in service. Accordingly, the present portable unit allows for x-ray diffraction techniques to be used on parts where it is not practical or economic to remove them from service, such as cables or wire ropes used as tension members for bridges. Moreover, the preferred portable x-ray diffraction unit herein provides an easy to interpret readout of the results of its measurements by generating a map at the part site so that, for example, any abnormalities in stress measurements taken will be highlighted in comparison to adjacent points on the map where more normal measurements are shown.

In one form of the invention, an apparatus is provided having an x-ray head adjustable in at least three mutually transverse axes for directing x-rays from different positions toward a part. The apparatus includes a frame for supporting the x-ray head. An x-axis adjustment mount of the frame is provided and which is operably connected to the head for adjusting the head in an x-axis fore and aft direction. A y-axis adjustment mount of the frame is provided and which is operably connected to the head for adjusting the head in a y-axis lateral direction. A z-axis adjustment mount of the frame is provided and which is operably connected to the head for adjusting the head in a z-axis vertical direction. Accordingly, the present x-ray diffraction apparatus is significantly improved in terms of its ability to coordinate movements of the head in three different axes of movement so that it can scan across a region of a part and direct x-rays thereat from different positions for taking measurements at a larger range of positions on the part than had been available via prior x-ray diffraction equipment. As the adjustment mounts are preferably integrated with the frame that supports the x-ray head, there is little need for operator intervention to move the part to reach the different points thereon from which measurements are desired to be taken.

In one form, the frame includes a fixture portion that is adapted to removably attach the frame to the part to allow the x-ray head to be used on parts in the field. With the fixture portion attached to the part to be measured, an operator merely has to initialize the x-ray diffraction unit for taking the desired measurements and otherwise need not intervene during the operation of the unit. This is in contrast to prior art x-ray diffraction equipment which requires an operator to hold the unit in position with respect to the part while the measurements are taken.

In another form, the fixture portion includes adjustable clamps for removably attaching the frame to different sizes of cables with the adjustable clamps comprising the y-axis adjustment mount to allow the head to be located at different positions along the length of the cable. The adjustable clamps for the fixture portion are advantageous as they do not require a different fixture to be constructed for each different part that is to be measured. Instead, the adjustable clamps can be used on cables of a variety of sizes for attaching the frame thereto.

In one form, the x, y and z adjustment mounts include linear drives for linearly adjusting the head in three mutually perpendicular directions with the x and y adjustment mounts allowing the head to direct x-rays to a predetermined region on the part and the z adjustment mount allowing the focal distance of the head from the part to be adjusted.

In another form, the frame and x, y and z adjustment mounts are integrated in a portable x-ray diffraction unit for being transported to different part sites. A stand distinct from the portable unit is provided for supporting the unit a desired part site. The integrated portable x-ray diffraction unit herein allows for measurements to be taken from parts in the field and from different points on the part by way of the integrated adjustment mounts.

It is preferred that the unit and the stand have an adjustable attachment therebetween to allow the unit and stand to be shifted to different positions relative to each other.

In a preferred form, the head includes detectors for sensing the x-rays off from the part. A controller is provided connected to the head for receiving signals from the detectors and including circuitry adapted to generate maps of a strength related characteristic of the part at the part site with the strength related characteristic being based on the received signals.

In another form, the head includes an elongate housing having a longitudinal axis, and the frame includes an r-axis adjustment mount operably connected to the head for adjusting the head in an r-axis rotary direction about the housing axis to allow the head to direct x-rays at contoured parts. Preferably, the frame includes a phi-axis adjustment mount operably connected to the head for adjusting the head in a phi-axis rotary direction transverse to the r-axis rotary direction. The phi-axis adjustment mount can be disposed forwardly in the x-axis direction from the z-axis adjustment mount.

In a preferred form, a touch sensor is provided which is shifted into engagement with the part with the head a predetermined distance from the part in the z-axis direction. A controller is signaled by the touch sensor for repeatable locating of the head at the predetermined distance from the part after use of the sensor. Preferably, the controller includes a teach mode to allow and operator to shift the touch sensor into engagement with the part at various locations thereon by shifting of the head via the adjustment mounts for mapping part contour so that the head precisely directs x-rays toward the part at the various locations along its contour.

In another form of the invention, an apparatus is provided for directing x-rays at parts with curved surfaces. The apparatus includes an x-ray head having an elongate housing including a longitudinal axis thereof, and a frame for supporting the x-ray head. An adjustment mount of the frame allows the head to undergo rotary movement about the longitudinal axis thereof to substantially keep the head at a predetermined distance from a curved surface of a part at which x-rays are directed at various positions along the part curved surface. Prior x-ray diffraction equipment has been limited to taking measurements from flat, planar surfaces. Where the part includes a curved surface, an operator would have to physically shift or rotate the part to allow the x-ray head to direct x-rays at different positions therealong. In contrast, the present apparatus including the adjustment mount for rotating the head about the housing axis allows the head to take measurements at various positions along the part curved surface while maintaining a substantially constant distance therefrom.

Preferably, a plurality of other adjustment mounts are provided for moving the head in a plurality of different directions so that the head moves in a path that substantially matches the contour along the part defined by the different positions at which x-rays are to be directed. As described more fully hereinafter, the contour of the part can be mapped into the memory of the controller which can then coordinate the operation of the adjustment mounts to allow the head to move in a path that keeps it at constant distance from the part despite complex shapes of its contour that may be present.

In another aspect of the invention, a method for obtaining strength related characteristics of a part is provided. The method includes providing a portable x-ray diffraction unit including an x-ray head having integrated adjustment mechanisms for shifting the head in a plurality of different directions, transporting the portable unit to a site at which the part is in service, orienting the x-ray head relative to the part for directing x-rays thereat, shifting the x-ray head via the adjustment mechanisms to direct x-rays at various positions on the part for obtaining a sufficiently large distribution range of measurements of the desired part characteristics for proper strength analysis thereof, detecting the diffraction of the x-rays from the part at the various positions thereon, transmitting signals to a controller for the portable unit that are based on the detected x-rays, interpreting the signals in circuitry of the controller to render measurements of at least one strength related characteristic of the part, and generating a map at the part site of the part characteristics across the entire distribution range of measurements for the part.

By generating maps at the part site, a person can readily determine the areas of the measured region where the strength related characteristic is in either normal or abnormal ranges therefor. The present method using an x-ray head having integrated adjustment mechanisms and which is incorporated in a portable x-ray diffraction unit makes it possible to generate the maps on site at a part location.

BRIEF DESCRIPTION OF THE DRAWINGS

FIGS. 11A and 11B are a flow chart of a method in accordance with the present invention of teaching a controller for the x-ray diffraction unit the path in which the head is to travel to obtained the desired measurements from different positions on a part to be measured;

FIGS. 13A–13C are views of maps of residual stress of a part that can be generated in the field with the apparatus and method of the present invention.

DETAILED DESCRIPTION OF THE PREFERRED EMBODIMENTS

Figure 1:
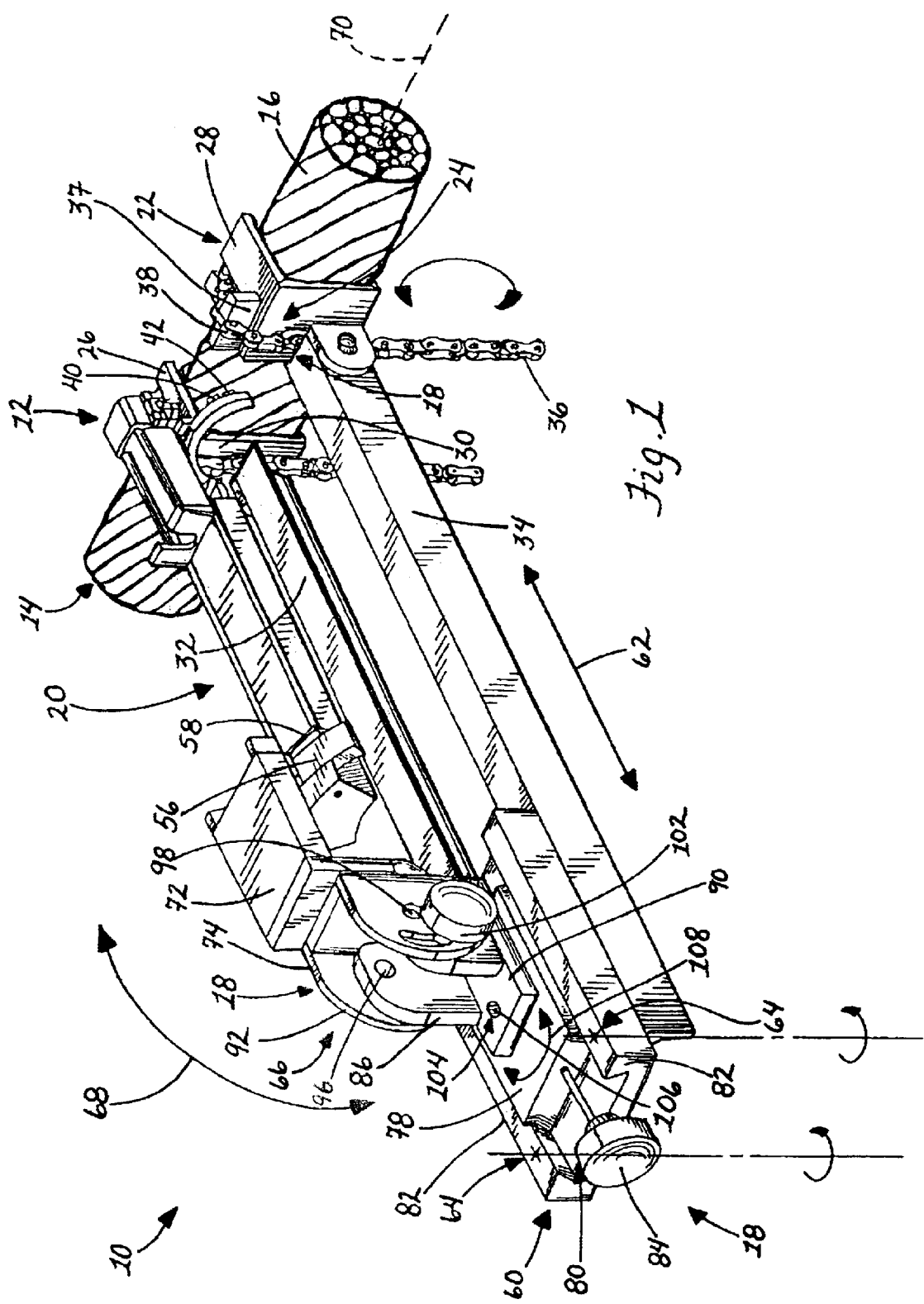
FIG. 1 is a perspective view of a portable x-ray diffraction apparatus including a frame having adjustable mounts for allowing an x-ray head to move in different directions and a fixture portion for attaching the frame of the unit to a bridge tension member to be measured.

In FIG. 1, an x-ray diffraction apparatus 10 in accordance with the present invention is shown. The apparatus 10 includes an x-ray head 12 from which x-rays are directed at a part 14, such as the illustrated bridge tension member 16. The main advantage provided by the present apparatus 10 is in the ability of the x-ray head 12 to be moved in a plurality of different directions relative to the part via various adjustment mounts, generally designated 18, that are provided on frame structure 20 supporting the x-ray head 12 for its movements. In this regard, the adjustment mounts 18 afford the head 12 a range of movement so that the head 12 can direct x-rays at the part from different positions thereof and at corresponding different positions on the part 14. As discussed, this is particularly helpful where the part 14 is in service and subject to various use and environmental conditions that can cause highly specific and localized variations in the strength-related characteristic being measured by the x-ray defraction apparatus 10. By having the ability to scan a region of the part, aberrations in the characteristic being measured by the apparatus 10 can be readily determined so, for instance, such localized variations will not unduly influence the determination as to the remaining useful life of the part 14. By way of example and not limitation, the adjustment mounts 18 herein can provide the x-ray head 22 with movements in the range of 2 to 4 inches.

In the preferred and illustrated form of FIG. 1, the apparatus 10 is a portable unit that can be transported to a site at which the part 14 is in service. As shown, the portable apparatus 10 includes a fixture portion 22 at the front thereof which enables the frame 20 to be removably attached to the bridge cable or wire rope 16. In this manner, the portable x-ray apparatus 10 can be taken to the bridge and mounted to the cable 16 so that measurements can be taken therefrom without requiring it be removed from service or that the operator hold the apparatus 10 while the measurements are taken. In addition, the apparatus 10 allows measurements to be taken in conditions where due to loading or environmental reasons, the bridge tension member 16 is moving or vibrating. The fixture portion 22 is designed such that it does not introduce or attenuate the axial strain experienced by the wire rope or cable.

The fixture portion 22 allows easy positioning of the apparatus 10 relative to the bridge tension member 16 and is suitable for a wide range of wire rope and cable bundle sizes. To this end, the fixture portion 22 includes a pair of adjustable clamps 24. The adjustable clamps 24 of the fixture portion 22 allow the apparatus 10 to be used on tension members 16 having a wide variety of sizes without requiring a different fixture each time the tension member that is to be measured changes in diameter or configuration over a previously measured member 16. The adjustable clamps 24 each include a right angle bracket member 26 having an upper plate portion 28 and a vertical rear plate portion 30. Arms 32 and 34 of the frame 20 are attached at the forward ends as by welding or the like to the rear plate 30 of the clamps 24. Tightening members in the form of chains 36 are provided to adjustably tighten the clamps 24 onto the bridge tension member 16. The chains 36 run over an upstanding guide 37 near the juncture of the bracket plates 28 and 30 and around the tension member 16, as can best seen in FIG. 2. To tighten the clamps 24 onto the tension member 16, free ends 38 of the chains 36 are pulled to draw the chains 36 tight about the tension member 16 and bracket 26. A plastic protective sheet 39 can be wrapped on the tension member 16 to minimize damage thereto with the clamps 24 tightened thereon. Releasing the adjustable clamps 24 allows the portable apparatus 10 to be clamped onto various locations along the length of the tension member 16 and about its circumference, and can serve as one of the adjustment mounts 18 for coarse movement of the goniometer head 12 in, a lateral, y-axis direction, as will be more fully described hereinafter.

The x-ray diffraction apparatus 10 will next be more particularly described. The x-ray head 12 herein utilizes divergent x-ray optics that are preferably combined with a close proximity focus distance of approximately 30 to 40 millimeters, a predetermined sized aperture of the head 12 which results in an appropriately shaped divergent x-ray beam such as to illuminate the bridge tension member 16 as shown at 40 in FIG. 1, and a movable mask 42 which can limit the strain data measured, for example, to one wire rope or cable strand at a time. The mask 42 is specifically designed for the wire rope or cable 16 to be measured so that the curvature thereof has little or no effect on the measurements being taken via the x-ray head 12 herein.

The divergent x-ray optics provide better illumination of the material grains resulting in better definition of the diffraction peaks through increased counting statistics. The close proximity also reduces the attenuation of the x-ray signal both traveling to and from the object 14 being measured. In the case of textured materials and/or materials which exhibit preferred orientation of the material grains, better illumination is helpful and typically wire rope and cable strands 16 would be subjected to textured conditions by virtue of their fabrication process. Accordingly, the preferred short focal distance herein is particularly useful where the part 14 being measured is the illustrated bridge tension member 16.

In typical x-ray diffraction systems, the x-ray head 12 generates x-rays in an elongated housing 44 extending in a fore and aft x-axis direction along an internal, longitudinal axis 46 thereof A target anode (not shown) in the housing 44 directs x-rays out from the housing 44 through a collimator 48 at the lower, forward end thereof. The x-rays from the collimator 48 are directed at a specific point on the part 14 to be measured. Fiber optic detectors 50 are mounted on either side of the collimator 48 on an arcuate detector mount 52. Depending on the x-ray diffraction technique utilized, the x-ray head 12 can remain stationary while directing x-rays at the point on the part 14 from which measurements are desired, or the head can be oscillated in an arcuate path through a variety of tilt angles via a beta oscillation drive 54 (FIG. 5) so that the point on the part 14 is subject to multiple exposures by way of the multiple tilt angles at which the x-rays are directed at the part 14 from the head 12, and specifically the collimator 48 thereof As is known, the beta oscillation drive 54 can be of a rack and pinion variety, including an arcuate rack 56 that is driven in a similarly shaped slot of an arcuate slide bearing block 58.

The beta oscillation drive 54 typically is not designed for the x-ray head 12 to take measurements from different points on the part 14 absent movement of the part 14 itself or without manually holding and moving the head along the part 14 to the different positions. In this regard, the apparatus 10 of the present invention utilizes a plurality of adjustment mounts 18 that provide for either manual or automated movement of the x-ray head in a plurality of different directions without requiring that the part 14 be moved or that the operator hold the x-ray defraction apparatus at the different positions. The adjustment mounts 18 can include those that allow for both rough adjustments of the x-ray head 12 where high speed of movement and/or a large range of motion are desired, and for small, precision movements of the x-ray head 12 so that x-rays can be directed at different positions on the part 14 that are in close proximity to each other.

The frame 20 including the fixture portion 22 thereof in the apparatus 10 of FIG. 1 includes the following adjustment mounts 18: x-axis adjustment mount 60 for highly controlled movements of the x-ray head 12 in the fore and aft x-axis direction as indicated by arrow 62; rough x-axis adjustment mount 64 which allows for coarse movements of the x-ray head 12 in the x-axis direction 62; rough z-axis adjustment mount 66 which allows for coarse up and down movement of the x-ray head 12 in a pivotal z-axis direction indicated by arrow 68.

In a lateral y-axis direction such as along the bridge tension member axis 70, the previously described fixture adjustable clamps 24 can be utilized for coarse movements by releasing the clamps 24 and shifting the apparatus 10 along the axis 70. Alternatively, the rough x-axis adjustment mount 64 can be used as will be described hereinafter for coarser, larger movements of the x-ray head 12 in the axial direction of the member 16.

As can be seen in FIG. 1, the x-ray head 12 can be connected to the forward end of the bearing block 58 which, in turn, is connected to a bracket portion 72 of the frame structure 20. A clevis member 74 is connected to the rear of the bracket portion 72. A threaded adjustment rod 76 extends in the x-axis direction 62 into an x-axis slide 78 with the threaded rod 76 being rotatably mounted therein. The slide member 78 can have a dovetail shape for fitting in dovetail slot 80 of slide bearing block 82. An internally threaded nut (not shown) fixed relative to the rod 76, and the slide member 78 and block 82 can be provided so that rotating the enlarged knob end 84 of the adjustment rod 76 causes the member 78 to linearly slide in the x-axis direction 62 in the slot 80. The slide member 78 is operably connected to the x-ray head 12 at the forward end of the frame 20 by a pair of ears 86 upstanding therefrom and adjustably connected to the clevis member 74, as described more fully hereinafter.

For coarse movements along the x-axis direction 62, the rough x-axis adjustment mount 64 employs pivoting of the arms 34 about pivot members 88 attached to the rear of the arms 34. The bottom of the bearing block 82 is in sliding engagement with the tops of the arms 34 so that as the arms 34 are pivoted about their respective pivot members 88 in a direction away from each other, the bearing block 82 will be caused to slide forwardly along the tops of the arms 34, thus moving the head 12 in the x-axis direction 62. Bringing the arms 34 back toward their parallel disposition causes the bearing block 82 to slide rearwardly in the x-axis direction 62. To use the mount 64 to move the head 12 in the y-axis direction, both arms 34 are pivoted in the same direction while recognizing that this will also give the head 12 a component of movement in the x-axis direction due to the pivoting action of the arms 34 which will be imparted to the head 12. In addition, axial strains experienced by the bridge tension member 16 can be taken up by slight pivoting of the arms 34 which, although creating movement of the head 12, should be of a sufficiently minimal character so as not to cause errors during measurement.

As previously described, the ears 86 extend upwardly from the slide member 78. In this regard, a support member 90 is provided between the slide member 78 and the ears 86 with the ears 86 projecting upwardly therefrom. The ears 86 are spaced laterally from each other so that they fit between rearwardly extending arms 92 of the clevis member 74. The arms 92 and ears 86 are secured by way of quick disconnect pins 94 extending through aligned apertures 96 and 98 thereof.

The rough z-axis adjustment mount 66 is formed by arcuate slots 100 provided in each of the clevis arms 92 and through which adjustment screws 102 extend and into the ears 86. Accordingly, to make coarse adjustments in the z-axis direction 68, the quick disconnect pins 94 are pulled and the adjustment screws 102 are loosened. This allows the position of the x-ray head 12 to be adjusted in the z-axis direction 68 by pivoting thereof in a substantially vertical direction until at the desired vertical distance from the part 14 from which measurements are to be taken. Once in the proper position, the adjustment screws 102 can be tightened in their adjusted positions in the slots 100 with the pins 94 reinserted in the apertures 96 and 98. As is apparent, because of the pivoting action, there is a fore and aft x-axis component of movement associated with the coarse vertical movement in the z-axis direction 68.

The apparatus 10 of FIG. 1 also includes a rough phi-axis adjustment mount 104 to allow the x-ray head 12 to be pivoted about a vertical axis. As shown in FIG. 1, the phi-axis adjustment mount 104 is formed by a pivot member 106 which allows the support member 90 to be pivoted relative to the slide member 78 in a rotary phi-axis direction as indicated by arrow 108. In this manner, the x-ray head 12 can be provided with compound x-y axes movement via the phi-axis adjustment mount 104.

Figure 2:
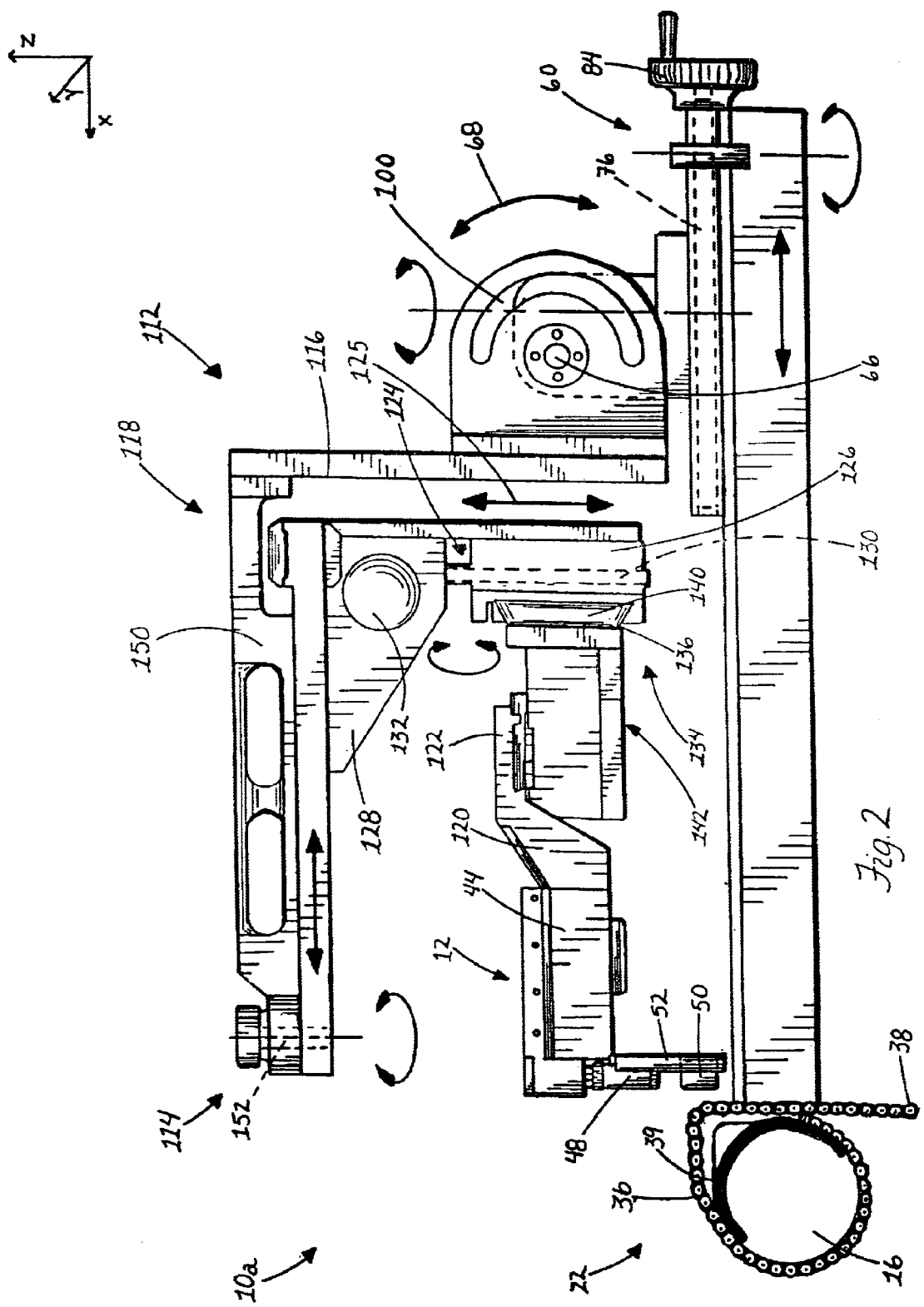
FIG. 2 is a side-elevational view of a portable unit similar to FIG. 1 including integrated x, y, z, r and phi adjustment mounts for moving the x-ray head in respective x, y, z, r and phi axes corresponding to the different mounts.
Figure 3:
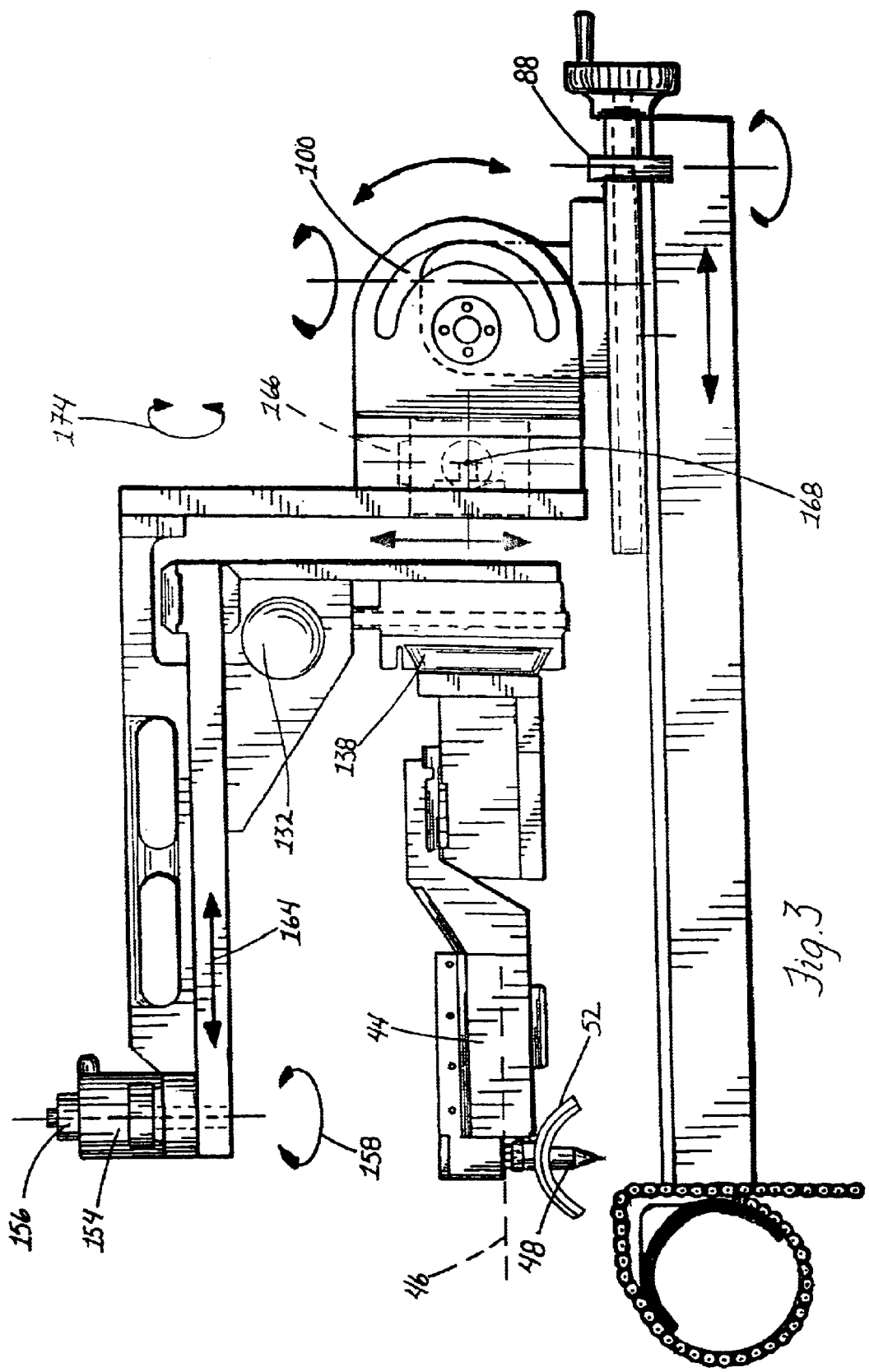
FIG. 3 is a view similar to FIG. 2 showing a goniometer and detector mount of the x-ray head rotated 90 degrees from the FIG. 2 position.
Figure 4:
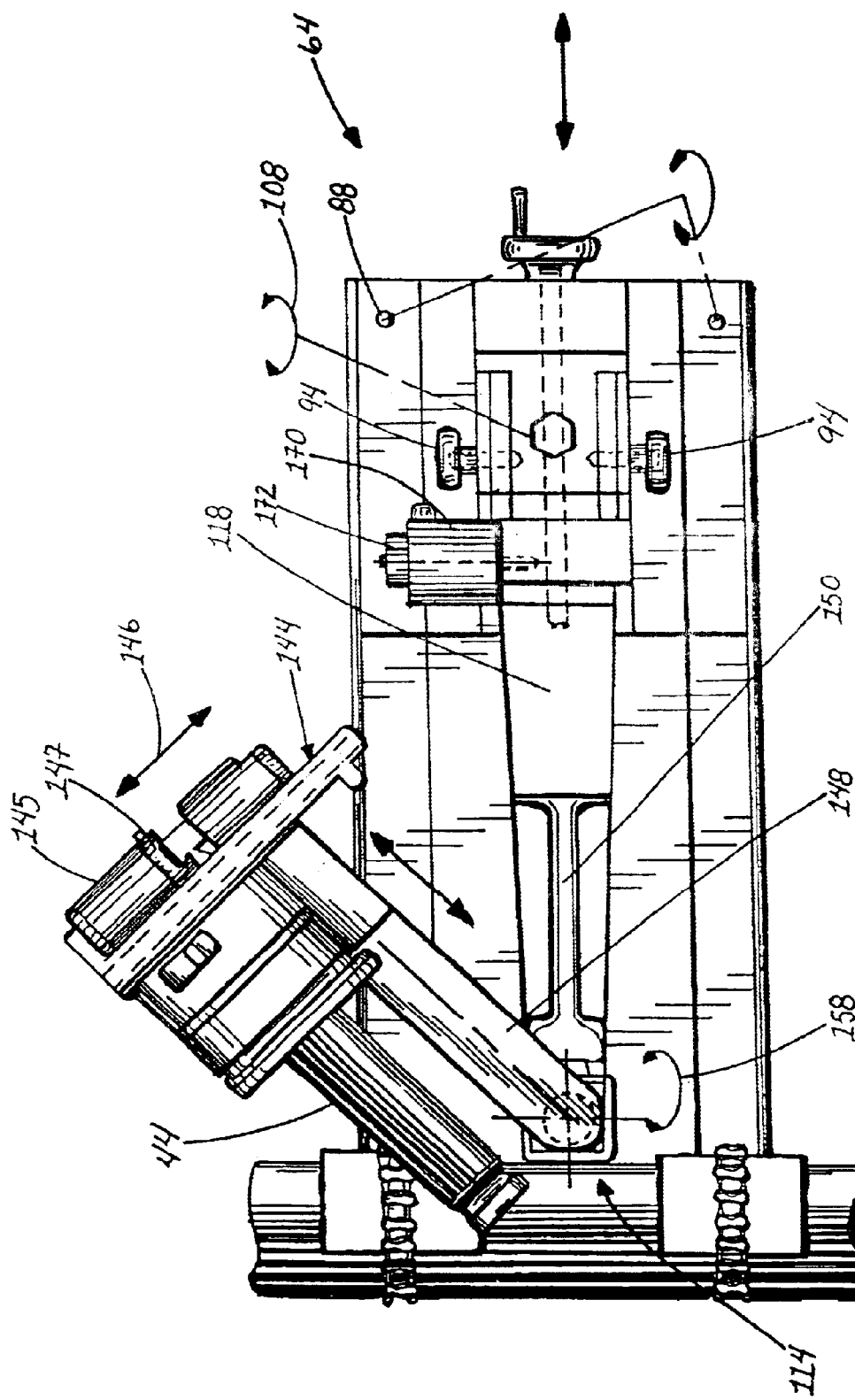
FIG. 4 is a plan view of the portable unit of FIGS. 2 and 3 showing the x-ray head rotated about the phi axis.

FIGS. 2–5 are directed to an apparatus 10a similar to apparatus 10 in that the x-ray head 12 thereof is capable of movements in a plurality of different directions. It also is preferably adapted to be portable and mounted to a bridge tension member 16 via fixture portion 22 thereof As best seen in FIG. 4, the rough x-axis adjustment mount 64 is substantially the same as previously described. Similarly, the rough z-axis adjustment mount 66 is also similar to that previously described for apparatus 10. The x-axis adjustment mount 60 of apparatus 10 is substantially the same in apparatus 10a; however, an additional fine x-axis adjustment mount 110 is incorporated in frame 112 of the apparatus 10a so that both coarse and precision measurements of the head 12 can be made in the x-axis direction 62. Also, a fine phi-axis adjustment mount 114 is incorporated in the frame 112.

As can be seen in FIGS. 2 and 3, the frame 112 includes a vertical wall portion 116 and a horizontal wall portion 118 connected at the top of the wall portion 116 and projecting forwardly therefrom. The horizontal wall portion 118 generally extends above and overhangs the x-ray head 12 with the x-ray head 12 cantilevered out from the bottom of the vertical wall portion 116 by a rearwardly extending support arm 120 connected to the rear of the x-ray head housing 44 at its forward end and to mounting portion 122 at the rear thereof with the mounting portion 122 being offset from the housing axis 46.

Figure 12:
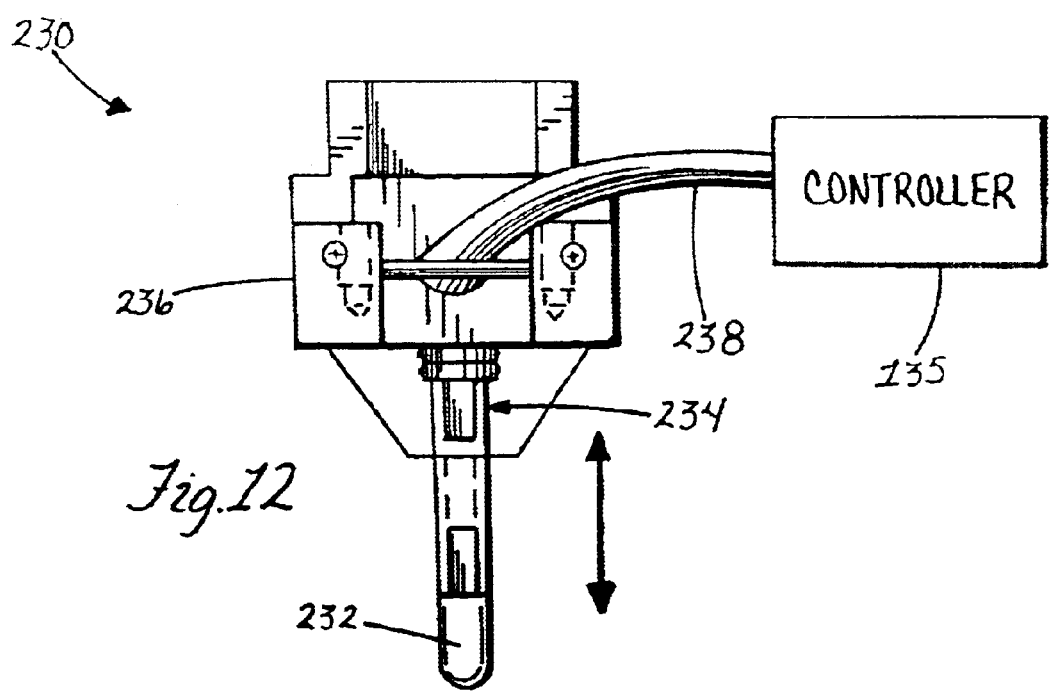
FIG. 12 is a elevational view of the part sensor for use in the autofocus and teach map methods of the present invention.

The apparatus 10a further includes a fine z-axis adjustment mount 124 incorporated in the frame 112 for moving the x-ray head 12 in a vertical z-axis direction as indicated by arrow 125. This is in addition to the as previously described rough z-axis adjustment mount 66 which allows for coarser pivoting movement of the x-ray head 12 in an up and down fashion along an arcuate path as indicated by arrow 68. Z-axis drive block 126 is attached to the frame 112 near the bottom of the vertical wall potion 116 and a gusset 128 is attached between the wall portions 116 and 118 at the juncture thereof. A z-axis linear drive in the form of screw drive 130 is mounted in the z-axis drive block 126 with its upper end in the gusset portion 128. Where the z-axis drive 130 is automated, motor 132 therefor can be located in the gusset portion 128 and include an encoder 133 for providing precise position feedback information to a controller 135 (FIG. 12) which can be disposed in a control box (not shown) remote from the apparatus 10a to provide a closed-loop feedback system for automated movements of the x-ray head 12 herein. Accordingly, operation of the screw drive 130 causes the x-ray head 12, which is operably connected to the z-axis drive block 126, to shift in a vertical up and down direction 125 for providing small, precision movements of the head 12. In this manner, the precision movements provided to the head 12 by the z-axis drive 130 allows for precision tuning of the focal distance of the head 12 from the piece part 14 to be measured.

The frame 112 also incorporates a fine y-axis adjustment mount 134. More particularly, the drive block 126 includes a dovetail slot 136, and a y-axis slide member 138 has a rear dovetail portion 140 which mates in the dovetail slot 136. The fine y-axis adjustment mount 134 is operably connected to the x-ray head 12 by way of cantilevered portion 142 extending forwardly from the y-axis slide member 138 and attached to the bottom of the mounting portion 122 of support arm 120. A y-axis linear drive in the form of screw drive 144 is provided, as can be seen in FIG. 4. Where the y-axis drive 144 is automated, y-axis motor 145 is provided including an encoder 147 similar to the z-axis motor 132. Accordingly, operation of the screw drive 144, either manually or automatically if it is motorized, causes the head 12 to move in a lateral, y-axis direction 146. For the phi-axis adjustment mount 114, the horizontal wall 118 includes a lower wall portion 148 that is pivotal relative to upper wall or handle portion 150. In this regard, operation of the y-axis screw drive 144 causes the housing 44 to shift laterally relative to the wall portion 148 thereabove, as can be seen in FIG. 4.

The fine phi-axis adjustment mount 114 is provided at the forward end of the wall portion 118 and includes a pivot drive member 152 pivotally interconnecting the lower and upper wall portions 148 and 150. Where automated, the phi-axis adjustment mount 114 includes motor 154 and associated encoder 156. Accordingly, operation of the phi-axis pivot drive member 152 causes pivoting of the wall portion 148 relative to the wall portion 150 about rotary phi-axis indicated by arrow 158. This is in addition to the rotary movement provided by phi-axis adjustment mount 104 in rotary direction 108 about a pivot axis that is rearwardly of the pivot axis of the rotary direction 158.

Figure 5:
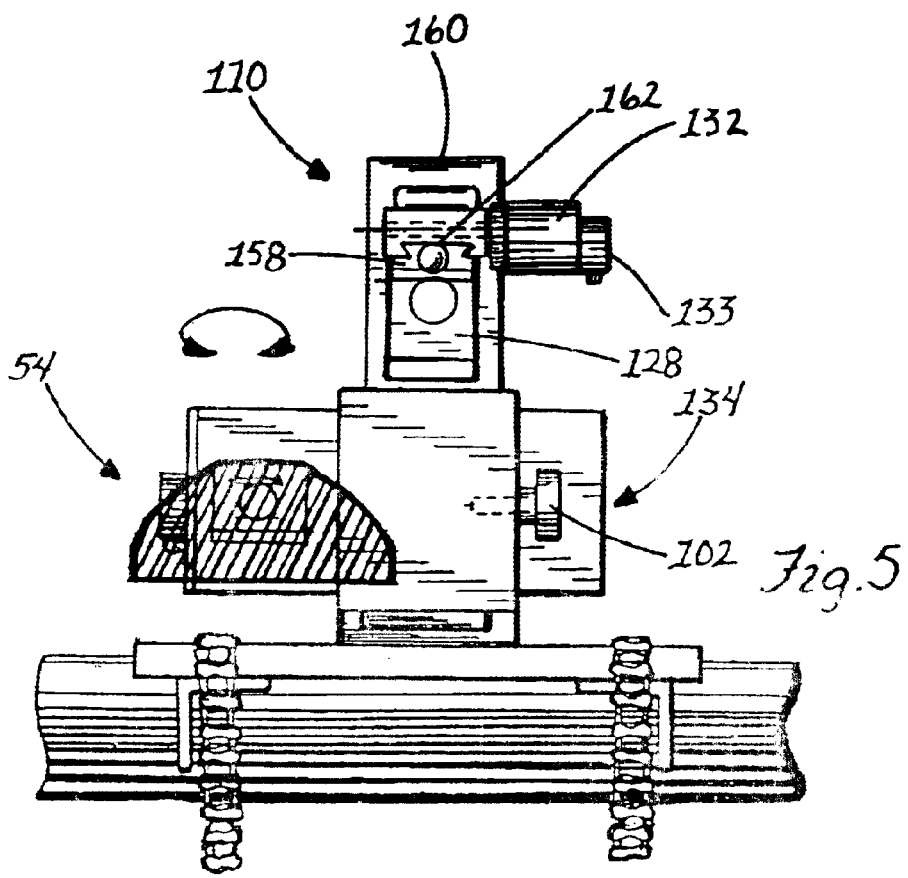
FIG. 5 is a front elevational view of the portable unit of FIGS. 2–4 showing an arcuate oscillation drive for the x-ray head.

The fine x-axis adjustment mount 110 includes slide member 158 and slide bearing 160 which can have a dovetail mating fit with one another, as can be seen in FIG. 5. The slide member 158 can be provided on the gusset 128 with the bearing 160 formed in the lower wall portion 148. A linear x-axis drive in the form of screw drive 162 is provided in the slide 158, and where automated, includes a motor 132 and associated encoder 133. Operation of the x-axis screw drive 162 causes fine precision movements of the x-ray head 12 in the fore and aft, x-axis direction indicated by arrow 164 this movement is in addition to the coarse x-axis movement afforded by rough x-axis adjustment mount 64.

An r-axis adjustment mount 166 is also provided at the rear of the vertical wall portion 116 for rotating the x-ray head 12 about its axis 46. The r-axis adjustment mount 166 is operably connected to the head 12 via the structure between the frame wall portion 116 and the head housing 44 so that rotation of the housing 44 also entails rotation of the fine x-axis adjustment mount 110, fine phi-axis adjustment mount 114, fine z-axis adjustment mount 124, and fine y-axis adjustment mount 134. The r-axis adjustment mount 166 includes a rotary drive in the form of rotary member 168, and where automated, a motor 170 and associated encoder 172 for rotating the member 168 in a rotary r-axis direction as indicated by arrow 174.

The r-axis adjustment mount 166 is of particular value where curved surfaces exist on the part 14 such as pipes and the like so that rotation of the head 12 in the r-axis direction 174 keeps the head 12 at a substantially constant distance from the curved surface. In this manner, the r-axis mount adjustment 166 saves the time associated with the process of lifting the head 12 away from the part, rotating the curved surface and then bringing the head 12 back into the proper focused position relative to the part curved surface, and the potential for errors this process entails. Instead, the r-axis adjustment mount 166 allows the head 12 to be rotated about its axis 46 to track the curvature of the curved surface on the part 14 maintaining a substantially constant focused distance therefrom without requiring constant recalibration each time a different point on the part is to be measured.

In both apparatus 10 and apparatus 10a, the adjustment mounts 18 provide the head 12 the ability to be moved to different positions relative to the part 14 without moving the part itself. Both rough and fine adjustments mounts 18 are provided so that an operator can move to different regions on a part 14 in a rapid manner where accuracy is not as critical but speed of movement is more important, and then can use the fine adjustment mounts to precisely control head movement as it scans across a particular region on the part 14 between measurement points thereon. This combination provides for highly efficient and accurate measurements across a representative sampling of points on a part 14 so that determinations can be more accurately made with respect to the measured strength characteristic(s) of the part 14 and its remaining useful life. In addition to the advantage with respect to curved surfaces previously discussed, the movements of the head 12 in the x-, y- and z-axes allow for parts having multilevel surfaces to be measured without requiring operator intervention to move the parts 14, and the attendant time delays associated therewith, as described above. Accordingly, the present invention provides improved flexibility in terms of the types of parts 14 that can be efficiently measured and accurately characterized with the x-ray diffraction equipment described herein.

Figure 6:
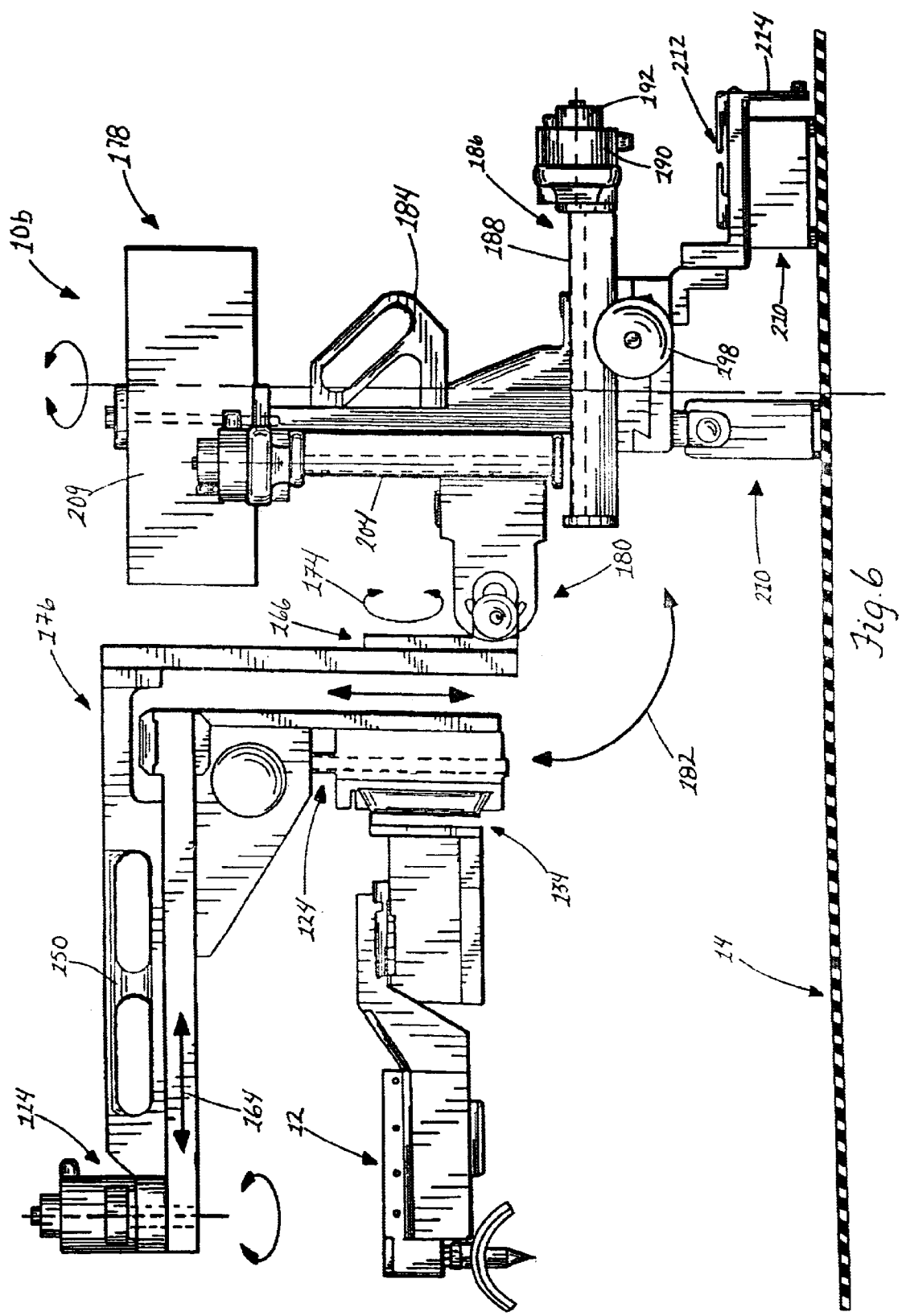
FIG. 6 is a side elevational view of another portable x-ray diffraction unit including adjustment mounts on a frame thereof for moving the x-ray head in different directions and showing a stand portion of the frame for supporting the unit at the part site.
Figure 7:
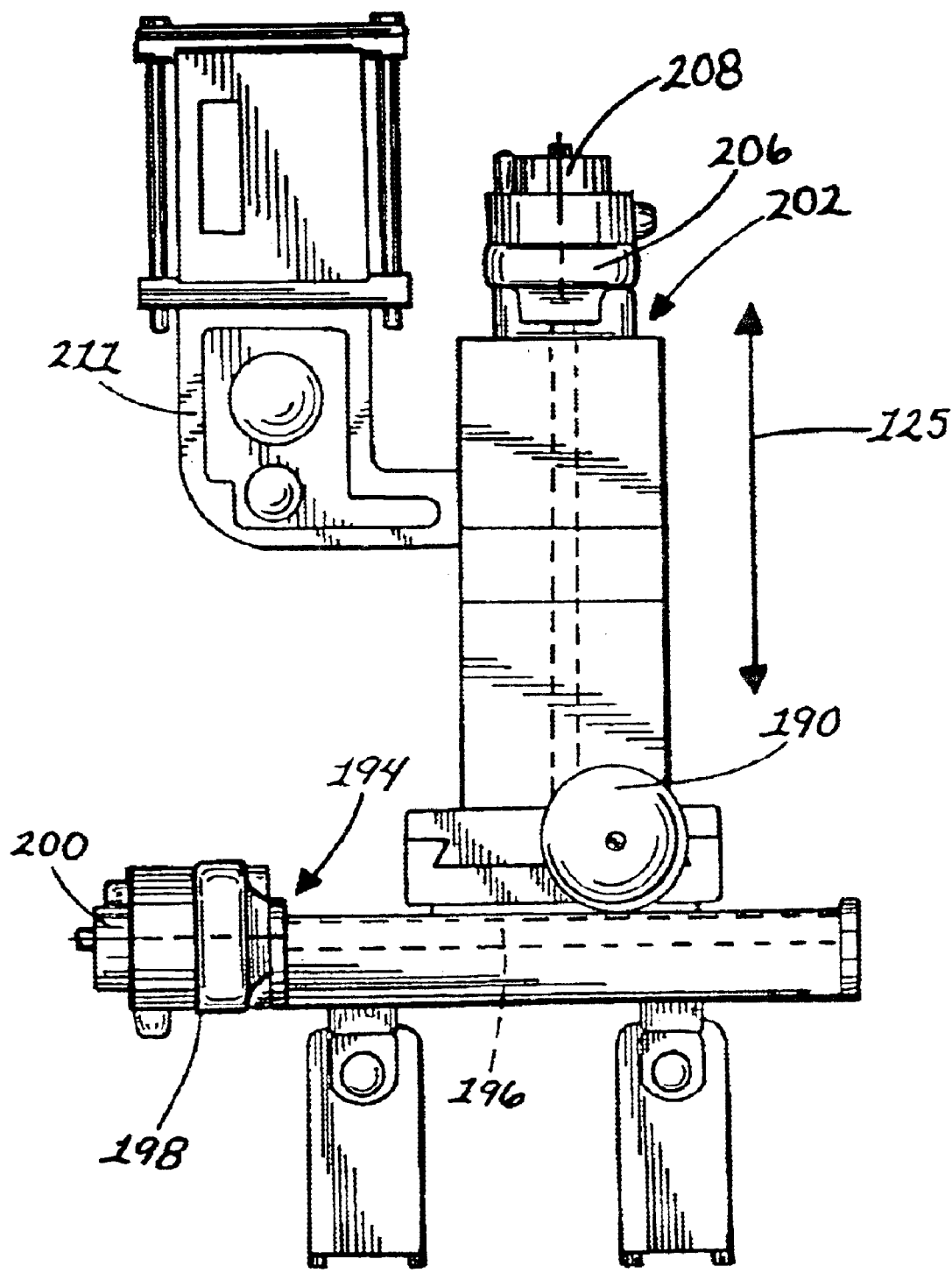
FIG. 7 is a front elevational view of the portable unit of FIG. 6 showing coarse y and z axes adjustment mounts of the stand for moving the head in corresponding y and z axes of movement.

Referring next to FIGS. 6 and 7, x-ray diffraction apparatus 10b is shown which is similar to those previously described although it lack the fixture portion 22 and instead is adapted more generally for measuring different types of parts, such as pipes. To this end, the apparatus 10b includes a forward measuring portion 176 including the x-ray head 12 and a rearward stand portion 178 that are distinct from each other and are interconnected via an adjustable connection 180 similar to the previously described rough z-axis adjustment mount 66 in both apparatus 10 and 10a. In this manner, the relative position between the measuring portion 176 and the stand portion 178 can be adjusted in a pivotal direction as indicated by arrow 182. The measuring portion 176 of the apparatus 10b incorporates substantially the same fine x-axis adjustment mount 110, fine phi-axis adjustment mount 114, fine z-axis adjustment mount 124, fine y-axis adjustment mount 134, and r-axis adjustment mount 166 as in the previously described apparatus 10a. Accordingly, the head 12 is capable of taking measurements from a large number of different positions in a region on the part 14 without necessitating movement of the part itself. Further, because of the distinct nature of the portions 176 and 178 of the apparatus 10b, the unit is highly portable and accordingly, both are provided with handles with the handle for the measuring portion 176 formed on upper wall portion 150 as in apparatus 10a, and the stand portion 178 including a handle 184, as best seen in FIG. 6.

Coarse movements of the x-ray head 12 can be provided by adjustment mounts 18 incorporated into the stand portion 178. A rough x-axis adjustment mount 186 includes an x-axis linear drive in the form of screw drive 188 which can be either manually operated or automated via motor 190 and associated encoder 192 thereof. Operation of the x-axis screw drive 188 will cause the head 12 to shift in the x-axis direction 164. Rough y-axis adjustment mount 194 is similarly constructed including a y-axis linear drive in the form of screw drive 196 which can be either manually operated or automated via motor 198 and associated encoder 200. Accordingly, operation of the screw drive 196 causes movement of the x-ray head 12 in the y-axis direction 146. Finally, rough z-axis adjustment mount 202 is provided on the stand portion 178 and includes a z-axis linear drive in the form of screw drive 204 that can be either manually operated or automated via motor 206 and associated encoder 208. Accordingly, operation of the linear drive 204 causes the x-ray head 12 to undergo coarse and rapid movement in the psi-axis direction 125.

As is apparent, each of the rough x-, y- and z-axes adjustment mounts 186, 194 and 202, respectively, shift the entire measuring portion 176 including all of the adjustment mounts thereof in the corresponding direction of movement. In this manner, the relative positions of the fine adjustments mounts will not change as the rough adjustment mounts 186, 194 and 202 are operated. Further, it will be noted that the construction of the rough and fine adjustments 18 are very similar in apparatus 10b. Accordingly, it is contemplated that their main distinction in terms of providing the head 12 with either coarse or fine, precision movements may be with respect to the speed at which they are operated.

It should be recognized that instead of the stand portion 178, a robot arm or the like could be utilized, particularly where the apparatus 10b is not required for field use. The robot arm could be controlled to give coarse movements to the measuring portion 176 to facilitate rapid movement of the head 12 to the general area from which x-rays are to be directed at the part to be measured.

FIGS. 6 and 7 also show a housing 209 connected to the stand portion 178 by bracket arm 211 with the housing 209 including the electronics for interpreting the signals received by the detectors 50. Mounting the housing 209 to the stand 178 as shown is desirable so that its heavy weight is not borne by the adjustment mounts and wo that it does not have to be moved by the associated drives thereof.

To mount the apparatus 10b to the part 14 being measured, a pair of magnetic feet 210 can be provided at the lower end thereof. The magnetic feet 210 can include permanent magnets for clamping the stand portion 178 tightly to the magnetic material of the part 14 which inactivated. In addition, the feet 210 can include a safety strap attachment 212 to provide additional support by a safety strap wrapped about the part 14 and pulled tight thereabout via crank arm 214 of the attachment 212.

Figure 8:
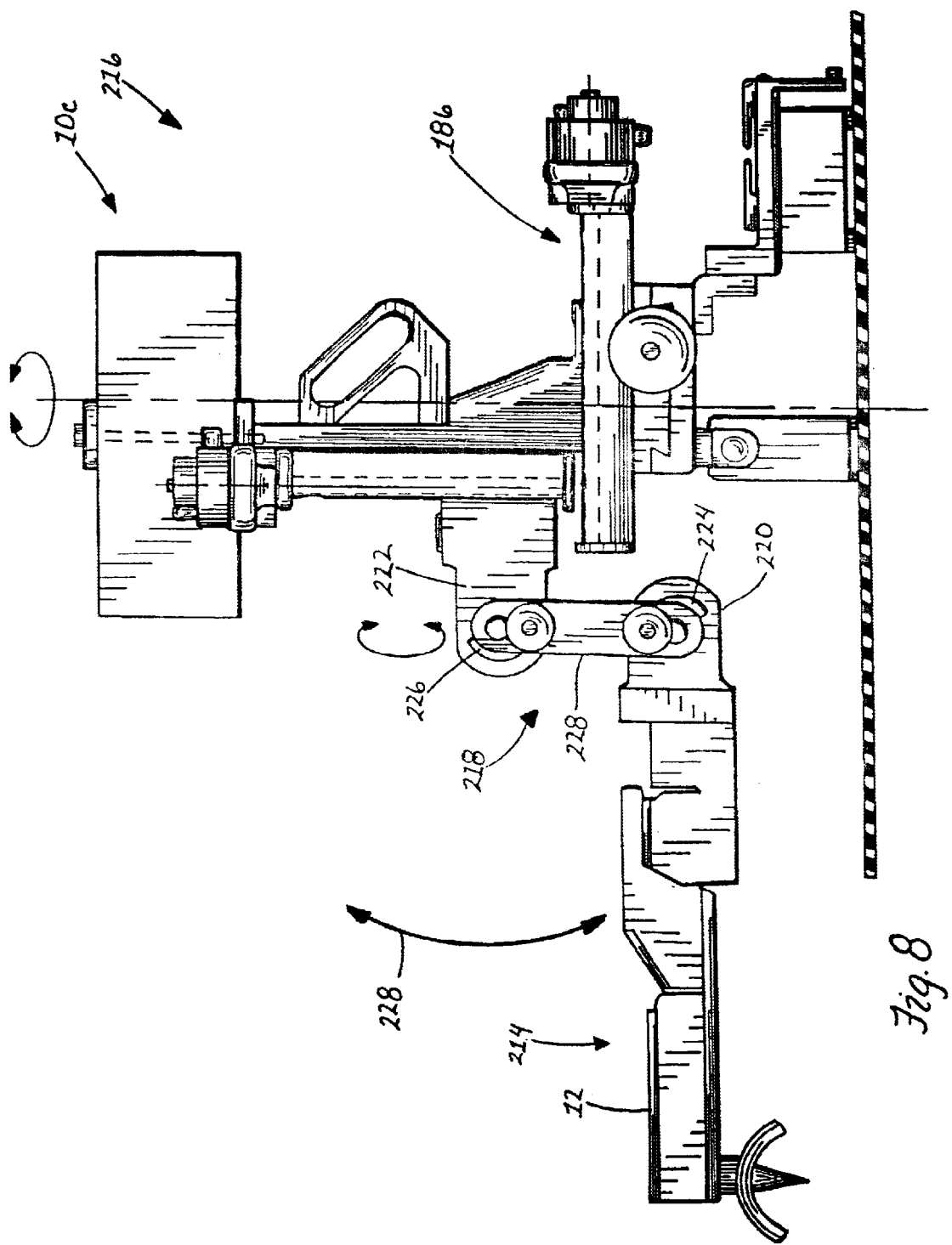
FIG. 8 is a side elevational view of another portable unit including a stand for supporting the unit a part site with adjustment mounts for moving the head in different directions.
Figure 9:
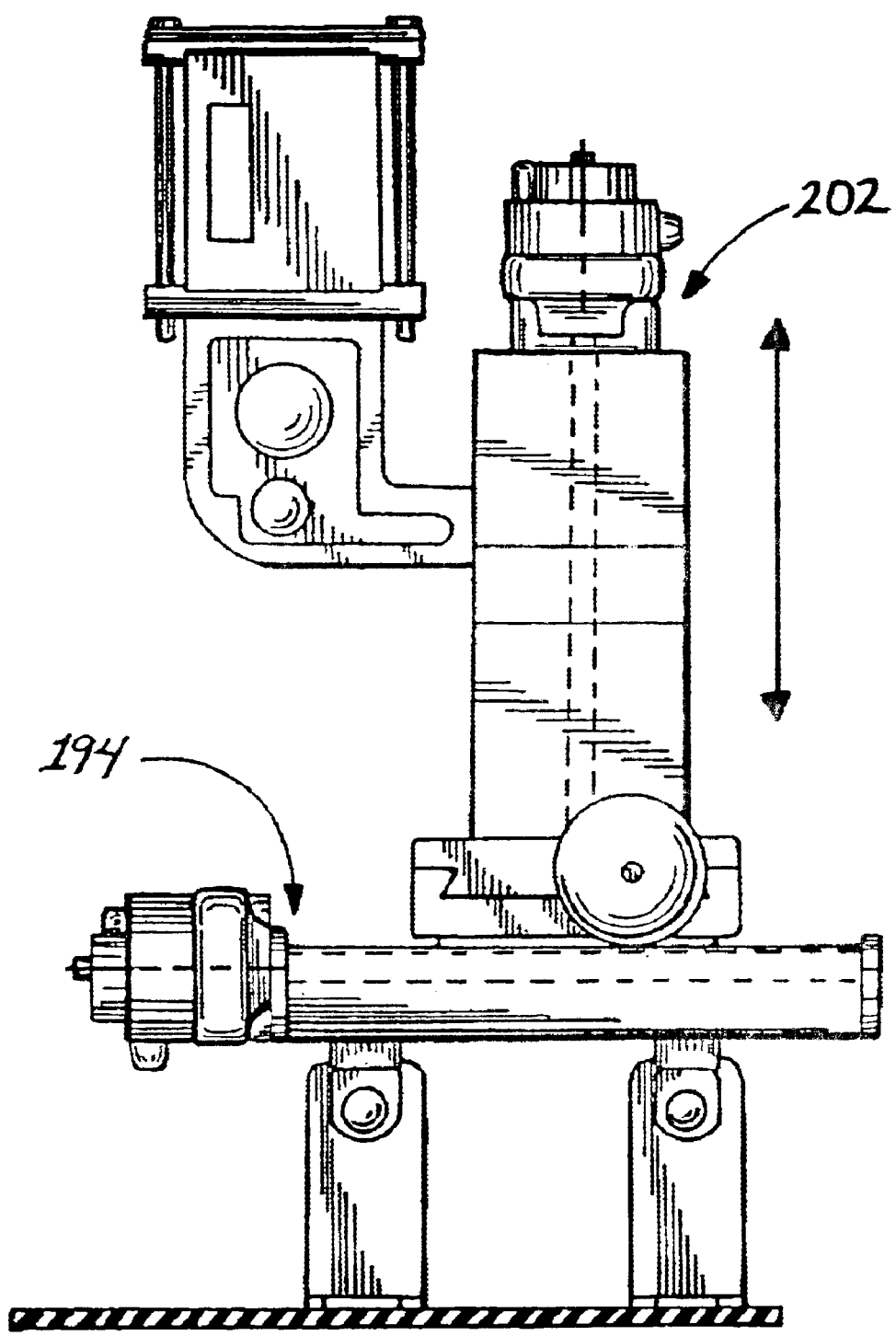
FIG. 9 is a rear elevational view of the unit and stand portion of FIG. 8 showing y and z axes adjustment mounts for moving the head in corresponding y and z axes of movement.

FIGS. 8 and 9 are directed to another x-ray diffraction apparatus 10c in accordance with the invention which also includes a forward measurement portion 214 including x-ray head 12 and a rearward stand portion 216 with an adjustable interconnection 218 therebetween similar to apparatus 10b. The adjustable interconnection 218 is slightly different in that both portions 214 and 216 include devises 220 and 222, respectively, in which respective arcuate slots 224 and 226 are formed. An interconnection link 228 extends between the devises 220 and 222 and can be fixed at various positions in the slots 224 and 226 at either end thereof. In this manner, the portions 214 and 216 can be pivoted in an arcuate up and down direction as indicated by arrow 228 with a so-called knuckling action provided by the wide range of relative positions they can assume based on the different positions the link 228 can be fixed in each of the slots 224 and 226.

The forward measuring portion 214 is significantly modified over that of x-ray diffraction apparatus 10b as the wall portions 116 and 118 of the frame 112 are absent due to the elimination of the adjustment mounts in the measuring portion 214. In this manner, the x-ray head 12 can more readily fit into confined spaces such as in the inside diameter of a pipe or in other openings of parts 14 including surfaces to be measured. Adjustments of the head 12 can be provided via the rearward stand portion 216 and the adjustment mounts thereof which are substantially the same as that described for apparatus 10b. In this regard, the stand portion 216 includes an x-axis adjustment mount 186, a y-axis adjustment mount 194 and a z-axis adjustment mount 202. In this instance, because of the lack of the fine adjustment mounts in the measuring portion 214, the speed of the associated motors of the respective adjustment mounts incorporated in the stand portion 216 can be reduced so as to improve the accuracy in moving the head 12 between positions to be measured as previously has been discussed. Accordingly, the mounts 186, 194 and 202 serve as both the rough and the fine adjustment mounts for the head 12 in apparatus 10c.

Figure 10:
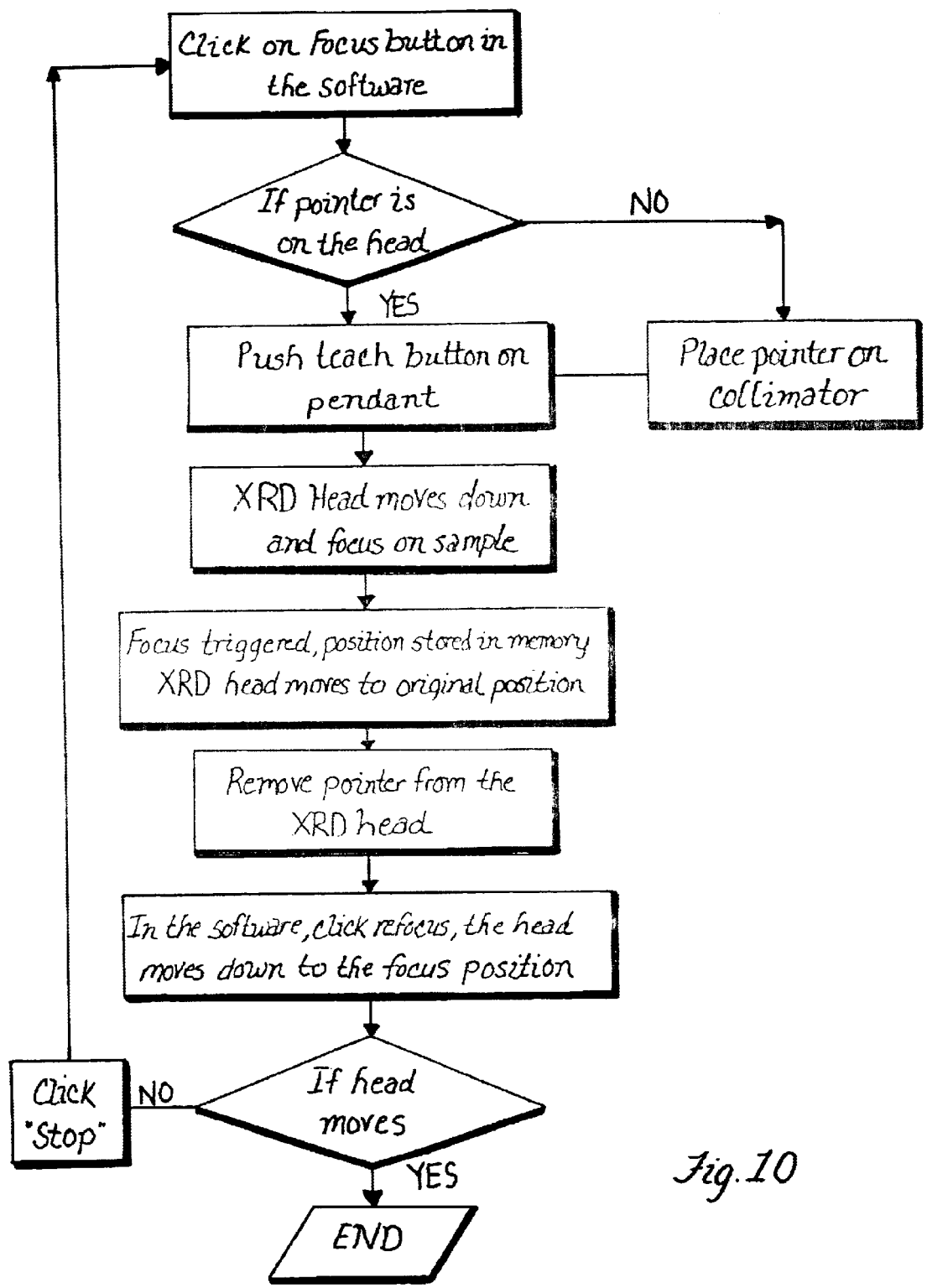
FIG. 10 is a flow chart of a method of providing for automatic refocusing of the head at a predetermined focus distance from the part to be measured.
Figure 11A:
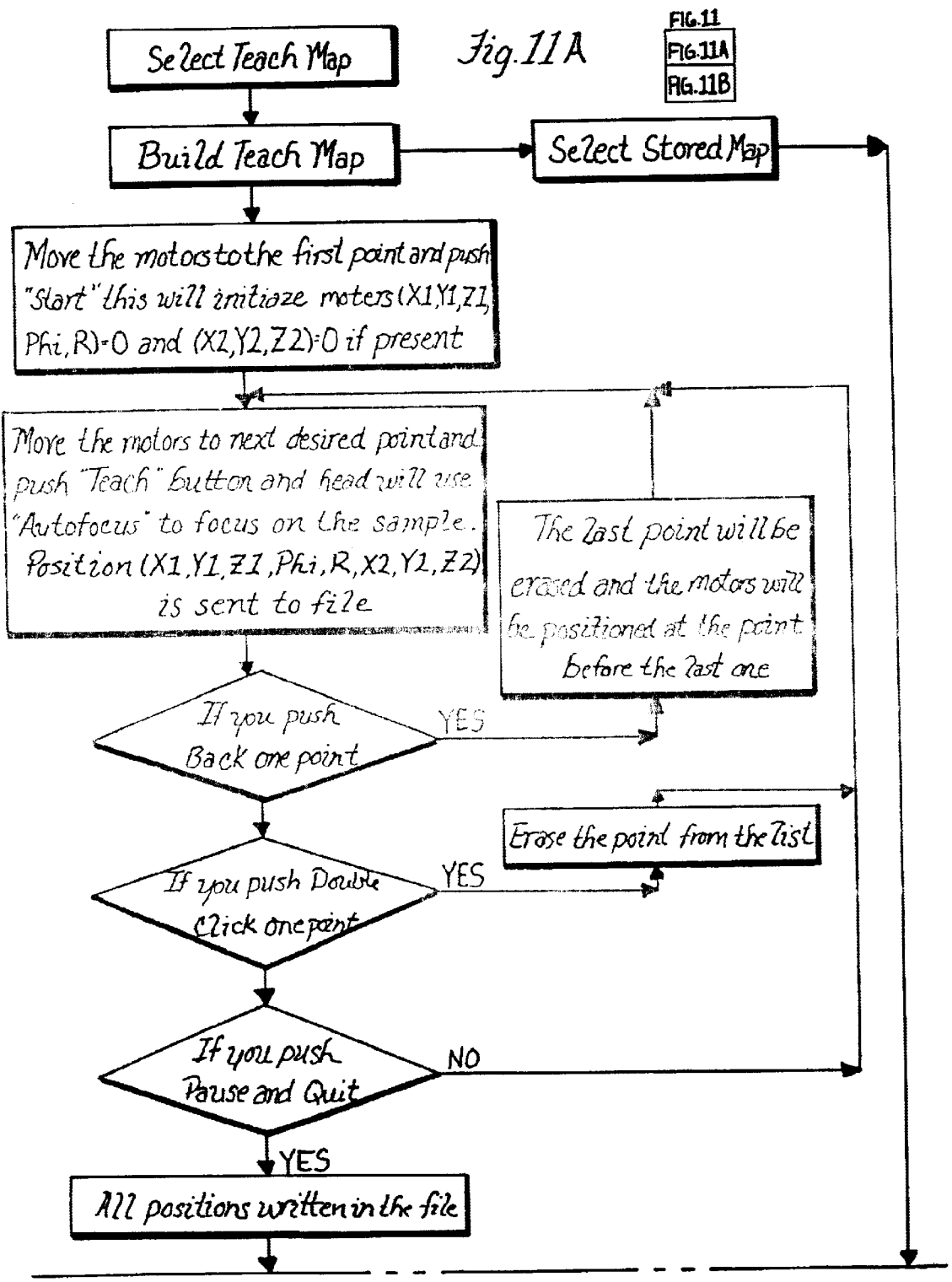

FIGS. 10, 11a and 11b show flow charts that depict methods for creating a map of the shape or configuration of the region or portion of the part 14 desired to be measured so that the head 12 can move under command of the controller 135 via the adjustment mounts 18 to the precise positions needed to have properly focused x-rays directed at the positions on the part to be measured. FIG. 10 shows how focusing can be accomplished using a part sensor in the form of touch sensor 230, shown in FIG. 12. The touch sensor 230 includes a probe 232 that when lowered into engagement with the part is depressed for actuating a microswitch 234 housed in the probe body 236. Circuitry in the sensor 230 detects the actuation of the switch 234 and signals the controller 135 by way of interconnect cable 238.

To use the touch sensor 230, it is removed from a stored position remote from the x-ray head 12 and placed onto the head 12 so that the probe 232 extends in a downward direction parallel to the collimator 48. An operator using a remote control box can coordinate movement of the head via the adjustment mounts and once in position lower the head 12 down until the probe 232 engages the surface of the part 14 to be measured. At this point, the head will be in its focus position at a predetermined distance defined by the length of the probe 232 from the part surface. Accordingly, for different focus distances, different length probes 232 can be utilized. Once the probe 232 engages the part surface, the controller 135 will receive the signal from switch 234 and store the position of the head 12 in memory, and in particular the positions of each of the adjustment mounts. Thereafter, the head 12 moves back to a home or initial position away from the part 12, and the touch sensor 230 is placed back in its stored position. At this point, all an operator has to do to focus the head 12 relative to the part surface is to click on a refocus icon in a Windows based program for instance or a "teach" key on the remote control box held by the operator and the head 12 under command of the controller 135 will automatically move back down to the previously determined focus position.

Referring next to FIGS. 11a and 11b, the software of the controller 135 can be programmed to allow the controller 135 to learn or be taught the contour on the region of the part surface from which measurements are desired. Although it is contemplated that the touch sensor 230 will be utilized for this purpose, it is also possible that the software can be adapted to accept and understand a digital interpretation of the part configuration, such as via a CAD drawing. To build the part configuration map in accordance with FIGS. 11a and 11b, the numerals 1 and 2 after the letters x, y, z indicate whether the motors are for the fine adjustment mounts (numeral 1) or for the rough adjustment mounts (numeral 2). To build the part map, the operator moves the head 12 by way of control over the adjustment mounts such as either via a PC Windows operating program or by controls on the remote control box. The operator moves the head to a position over each point on the part surface from which x-rays are to be directed thereat. At this position, the operator can actuate the "teach" key and the head will use the above-described "autofocus" routine to focus on he part surface. In a like manner, the operator will move the head 12 to the next position from which x-rays are to be directed at the next point on the part surface and initiate the "autofocus" sequence previously described. In this manner, each position of the head 12 will be stored in the controller so that the controller can command the head 12 to move in a precise path keeping the head 12 at a focused distance from the part positions to be measured. In addition, because of the use of the various adjustment mounts 18 as previously described, the x-ray diffraction equipment described herein can be made to automatically take measurements from fairly complex shapes without requiring any operator intervention.

Figures 13B, 13C:
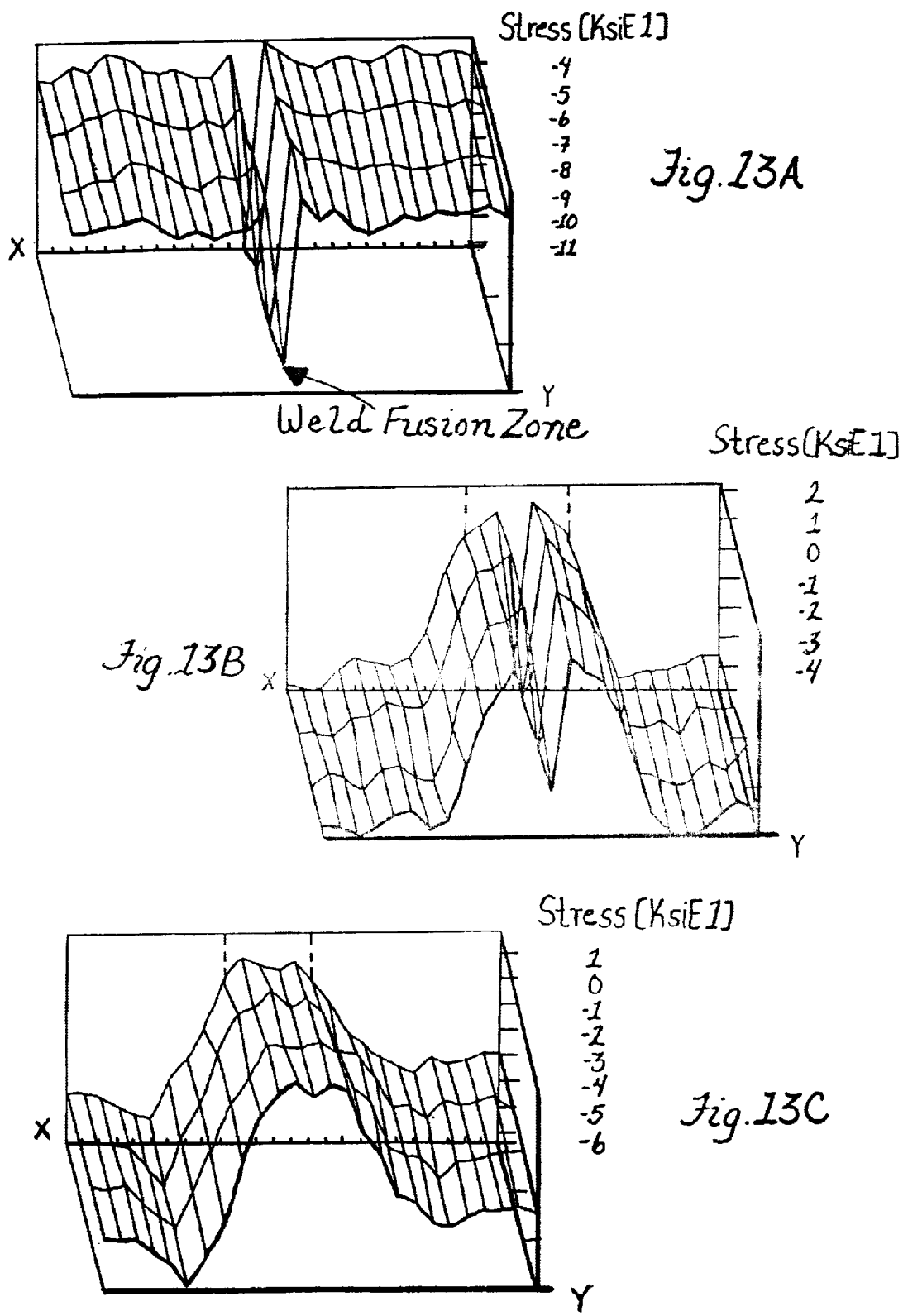

Further, where the equipment is used at a part site, it is desirable for the controller 135 to be adapted for generating maps of the measured strength characteristic so that an operator in the field can make ready comparisons of, for example, stress measurements to easily determine whether localized stress aberrations are present or more importantly if there undue tensile stresses that are more representative of overall fatigue affecting part life. As shown in the stress maps of FIGS. 13A–13C, the areas on the maps of FIGS. 13B and 13C between the vertical lines show undesirable tensile stresses in an easy to see fashion. By providing these types of maps to field personnel at their job site, it is anticipated that the value of the x-ray diffraction equipment will be unquestionably realized.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. An apparatus having an x-ray head adjustable in at least three mutually transverse axes for directing x-ray energy from different positions toward a part and sensing the energy from the part, the apparatus comprising:

at least one detector for sensing the x-ray energy;

a frame for supporting the x-ray head and the detector;

an x-axis adjustment mount of the frame operably connected to the head and detector for adjusting the head and detector in an x-axis fore and aft direction;

a y-axis adjustment mount of the frame operably connected to the head and detector for adjusting the head and detector in a y-axis lateral direction;

a z-axis adjustment mount of the frame operably connected to the head and detector for adjusting the head and detector in a z-axis vertical direction; and at least one fine adjustment mount of the frame operably connected to the head and detector for providing finer adjustments of the head and detector in one of the x, y and z directions than the corresponding one of the x, y and z-axis adjustment mounts to allow the head and detector to be moved rapidly via rough adjustments provided by the one adjustment mount, and to move more precisely via fine adjustments provided by the one fine adjustment mount.

2. The apparatus of claim 1 wherein the frame includes a fixture portion adapted to removably attach the frame to the part to allow the x-ray head to be used on parts in the field.

3. The apparatus of claim 2 wherein the fixture portion includes adjustable clamps for removably attaching the frame to different sizes of cables with the adjustable clamps comprising the y-axis adjustment mount to allow the head to be located at different positions along the length of the cable.

4. The apparatus of claim 1 wherein the x, y, and z adjustment mounts include linear drives for linearly adjusting the head in three mutually perpendicular directions with the x and y adjustment mounts allowing the head to direct x-rays to a predetermined region on the part and the z-adjustment mount allowing the focal distance of the head from the part to adjusted.

5. The apparatus of claim 1 wherein the frame and x, y, and z adjustment mounts are integrated in a portable x-ray diffraction unit for being transported to different part sites, and a stand distinct from the portable unit for supporting the unit at a desired part site.

6. The apparatus of claim 5 wherein the part and the stand have an adjustable attachment therebetween to allow the unit and stand to be shifted to different positions relative to each other.

7. The apparatus of claim 5 wherein the head includes detectors for sensing the x-rays off from the part, and a controller connected to the head for receiving signals from the detectors and including circuitry adapted to generate maps of a strength related characteristic of the part at the part site with the strength related characteristic being based on the received signals.

8. The apparatus of claim 1 wherein each of the x, y and z adjustment mounts comprise rough adjustment mounts, and the at least one fine adjustment mount comprises x, y and z fine adjustment mounts.

9. An apparatus having an x-ray head adjustable in at least three mutually transverse axes for directing x-ray energy from different positions toward a part and sensing the energy from the part, the apparatus comprising:

at least one detector for sensing the x-ray energy;

a frame for supporting the x-ray head and the detector;

an x-axis adjustment mount of the frame operably connected to the head and detector for adjusting the head and detector in an x-axis fore and aft direction;

a y-axis adjustment mount of the frame operably connected to the head and detector for adjusting the head and detector in a y-axis lateral direction; and a z-axis adjustment mount of the frame operably connected to the head and detector for adjusting the head and detector in a z-axis vertical direction and at least one fine adjustment mount of the frame for providing finer adjustments of the head and detector in one of the x, y and z directions than the corresponding one of the x, y and z-axis adjustment mounts to allow the head and detector to be moved rapidly via rough adjustments provided by the one adjustment mount, and to move more precisely via fine adjustments provided by the one fine adjustment, wherein the head includes an elongated housing having a longitudinal axis, and the frame includes an r-axis adjustment mount operably connected to the head for adjusting the head in an r-axis rotary direction about the housing axis to allow the head to direct x-rays at contoured parts.

10. The apparatus of claim 9 wherein the frame includes a phi-axis adjustment mount operably connected to the head for the adjusting the head in a phi-axis rotary direction transverse to the r-axis rotary direction.

11. The apparatus of claim 10 wherein the phi-axis adjustment mount is disposed forwardly in x-axis direction from the z-axis adjustment mount.

12. An apparatus having an x-ray head adjustable in at least three mutually transverse axes for directing x-ray energy from different positions toward a part and sensing the energy from the part, the apparatus comprising:

at least one detector for sensing the x-ray energy;

a frame for supporting the x-ray head and the detector;

an x-axis adjustment mount of the frame operably connected to the head and detector for adjusting the head and detector in an x-axis fore and aft direction;

a y-axis adjustment mount of the frame operably connected to the head and detector for adjusting the head and detector in a Y-axis lateral direction; and a z-axis adjustment mount of the frame operably connected to the head and detector for adjusting the head and detector in a z-axis vertical direction and at least one fine adjustment mount of the frame for providing finer adjustments of the head and detector in one of the x, y and z directions than the corresponding one of the x, y and z-axis adjustment mounts to allow the head and detector to be moved rapidly via rough adjustments provided by the one adjustment mount, and to move more precisely via fine adjustments provided by the one fne adjustment.

a touch sensor which is shifted into engagement with the part with the head a predetermined distance from the part in the z-axis direction, and a controller signaled by the touch sensor for repeatable locating of the head at the predetermined distance from the part after use of the sensor.

13. The apparatus of claim 12 wherein the controller includes a teach mode to allow an operator to shift the touch sensor into engagement with the part at various locations thereon by shifting of the head via the adjustment mounts for mapping part contour so that the head precisely directs x-rays toward the part at the various locations along its contour.

14. The apparatus of claim 13 wherein the head includes an elongate housing having a longitudinal axis, and the frame includes an r-axis adjustment mount operably connected to the head for adjusting the head in an r-axis rotary direction about the housing axis to allow the head to focus x-rays at parts having contours including curved surfaces without moving the part.

15. An apparatus for directing x-rays at parts with curved surfaces, the apparatus comprising:
- an x-ray head having an elongate housing including a longitudinal axis thereof;
- a frame for supporting the x-ray head; and
- an adjustment mount of the frame which allows the head to undergo rotary movement about the longitudinal axis thereof to substantially keep the head at a predetermined distance from a curved surface of a part at which x-rays are directed at various positions along the part curved surface.

16. The apparatus of claim 15 including a plurality of other adjustment mounts for moving the head in a plurality of different directions to allow the head to move in a pathe that substantially matches the contour along the part defined by the different positions at which x-rays are to be directed.

* * * * *

UNITED STATES PATENT AND TRADEMARK OFFICE
CERTIFICATE OF CORRECTION

PATENT NO. : 6,721,393 B1
DATED : April 13, 2004
INVENTOR(S) : Michael Brauss

It is certified that error appears in the above-identified patent and that said Letters Patent is hereby corrected as shown below:

Column 15,
Line 33, after "to" insert -- be --.

Column 16,
Line 19, before "adjusting" delete "the".
Line 36, after "direction;" delete "and".
Line 47, change "fne adjustment." to -- fine adjustment; --

Column 18,
Line 5, change "pathe" to -- path --.

Signed and Sealed this

Sixteenth Day of November, 2004

JON W. DUDAS
*Director of the United States Patent and Trademark Office*